United States Patent
Leghissa et al.

(10) Patent No.: US 10,682,110 B2
(45) Date of Patent: Jun. 16, 2020

(54) METHODS FOR PERFORMING DIGITAL SUBTRACTION ANGIOGRAPHY, HYBRID IMAGING DEVICES, COMPUTER PROGRAMS, AND ELECTRONICALLY READABLE STORAGE MEDIA

(71) Applicant: Siemens Healthcare GmbH, Erlangen (DE)

(72) Inventors: Martino Leghissa, Wiesenthau (DE); Andreas Maier, Erlangen (DE); Bernhard Stimpel, Erlangen (DE); Christopher Syben, Cadolzburg (DE)

(73) Assignee: Siemens Healthcare GmbH, Erlangen (DE)

( * ) Notice: Subject to any disclaimer, the term of this patent is extended or adjusted under 35 U.S.C. 154(b) by 102 days.

(21) Appl. No.: 16/048,536

(22) Filed: Jul. 30, 2018

(65) Prior Publication Data

US 2019/0046145 A1 Feb. 14, 2019

(30) Foreign Application Priority Data

Aug. 8, 2017 (EP) .................................. 17185341

(51) Int. Cl.
*A61B 6/00* (2006.01)
*G01R 33/48* (2006.01)
(Continued)

(52) U.S. Cl.
CPC ............ *A61B 6/5205* (2013.01); *A61B 6/481* (2013.01); *A61B 6/504* (2013.01); *A61B 6/5247* (2013.01);
(Continued)

(58) Field of Classification Search
CPC ..... A61B 6/5205; A61B 6/504; A61B 6/5247; A61B 6/481; G01R 33/4812; G06T 7/11;
(Continued)

(56) References Cited

U.S. PATENT DOCUMENTS 8,023,732 B2 9/2011 Deuerling-Zheng et al.
2017/0103287 A1 4/2017 Han

FOREIGN PATENT DOCUMENTS

WO WO2013087210 A1 6/2013

OTHER PUBLICATIONS

Bentoutou, Y., et al., "An invariant approach for image registration in digital subtraction angiography." Pattern Recognition 35.12, pp. 2853-2865 (2002).

(Continued)

*Primary Examiner* — Christopher Wait
(74) *Attorney, Agent, or Firm* — Lempia Summerfield Katz LLC

(57) ABSTRACT

Methods for performing digital subtraction angiography of a region of interest of a patient are described herein. The methods include acquiring a filled image data set of the region of interest by x-ray imaging and creating an angiography image data set by subtracting a mask image data set from the filled image data set, wherein an x-ray imaging device for x-ray imaging and a further imaging device for at least one additional imaging modality are co-registered and operable to acquire image data in the same field of view, wherein the imaging devices are used to simultaneously acquire the filled image data set using the x-ray imaging device and an anatomy data set using the further imaging device and the mask image data set in derived from the anatomy data set in a conversion process, which converts additional imaging modality image data into virtual x-ray image data.

15 Claims, 2 Drawing Sheets

(51) Int. Cl.
    *G06T 7/11* (2017.01)
    *G06T 7/30* (2017.01)
    *G06T 5/50* (2006.01)

(52) U.S. Cl.
    CPC ............ *G01R 33/4812* (2013.01); *G06T 5/50* (2013.01); *G06T 7/11* (2017.01); *G06T 7/30* (2017.01); *G06T 2207/10084* (2013.01); *G06T 2207/10116* (2013.01); *G06T 2207/20224* (2013.01); *G06T 2207/30101* (2013.01)

(58) Field of Classification Search
    CPC ... G06T 7/30; G06T 5/50; G06T 2207/10084; G06T 2207/10116; G06T 2207/20224; G06T 2207/30101
    See application file for complete search history.

(56) References Cited

OTHER PUBLICATIONS

European Search Report for corresponding Application No. 17185341.9-1124, dated Mar. 5, 2018.

Fahrig, Rebecca, et al., "A truly hybrid interventional MR/X-ray system: Feasibility demonstration." Journal of Magnetic Resonance Imaging: An Official Journal of the International Society for Magnetic Resonance in Medicine 13.2, pp. 294-300 (2001).

Frysch, R. et. al., "Rigid Motion Compensation in Interventional C-arm CT Using Consistency Measure on Projection Data", in: MICCAI 2015, Part I, LNCS 9349, pp. 298-306 (2015).

Kapanen, Mika, et al., "T1/T2*-weighted MRI provides clinically relevant pseudo-CT density data for the pelvic bones in MRI-only based radiotherapy treatment planning." Acta Oncologica 52.3, pp. 612-618 (2013).

Navalpakkam, Bharath K., et al., "Magnetic resonance-based attenuation correction for PET/MR hybrid imaging using continuous valued attenuation maps." Investigative radiology 48.5, pp. 323-332 (2013).

Staring, Marius, et al., "Nonrigid registration with tissue-dependent filtering of the deformation field." Physics in Medicine & Biology 52.23, pp. 6879-6892 (2007).

Unberath, Mathias, et al., "Virtual single-frame subtraction imaging." Proc. Int. Conf. Image Form X-Ray CT. https://www5.informatik.uni-erlangen.de/Forschung/Publikationen/2016/Unberath16-VSS.pdf, pp. 1-4 (2016).

Wang, Ge, et al., "Vision 20/20: Simultaneous CT-MRI—Next chapter of multimodality imaging." Medical physics 42.10, pp. 5879-5889 (2015).

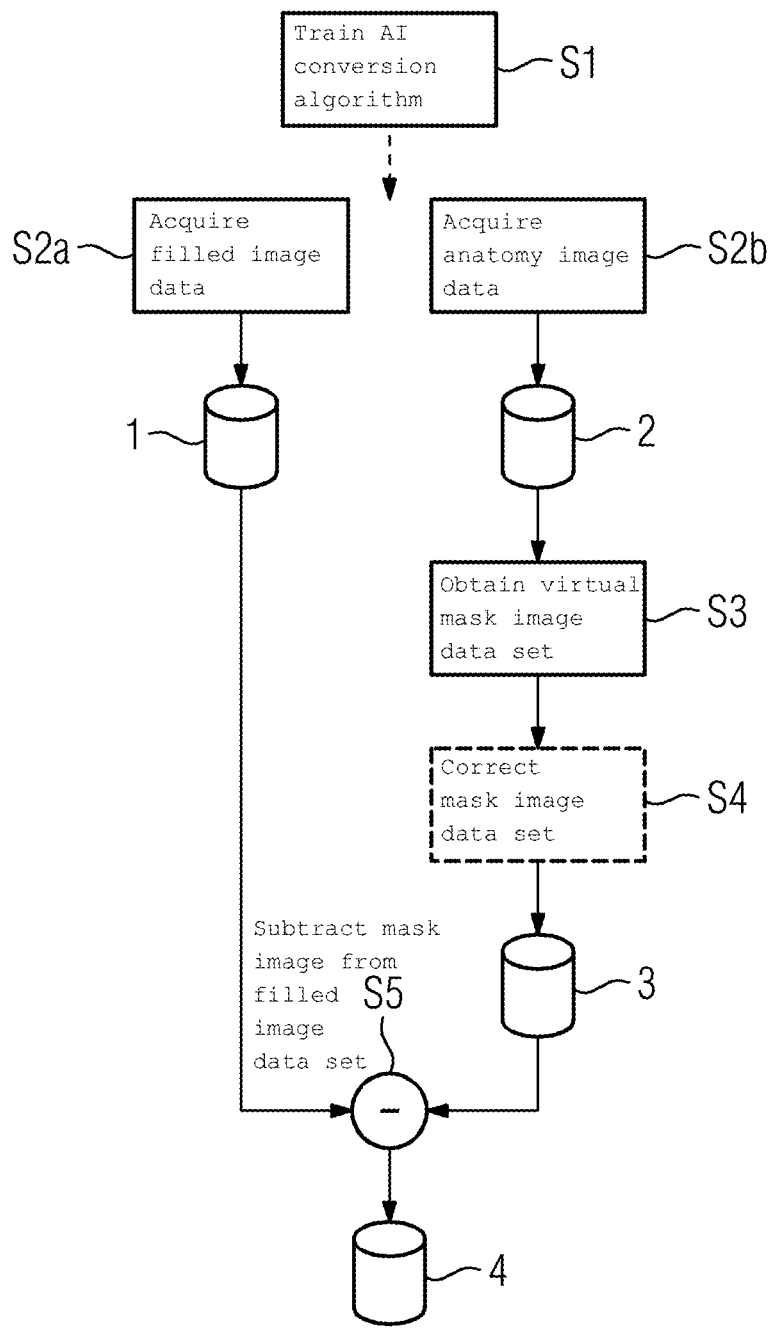

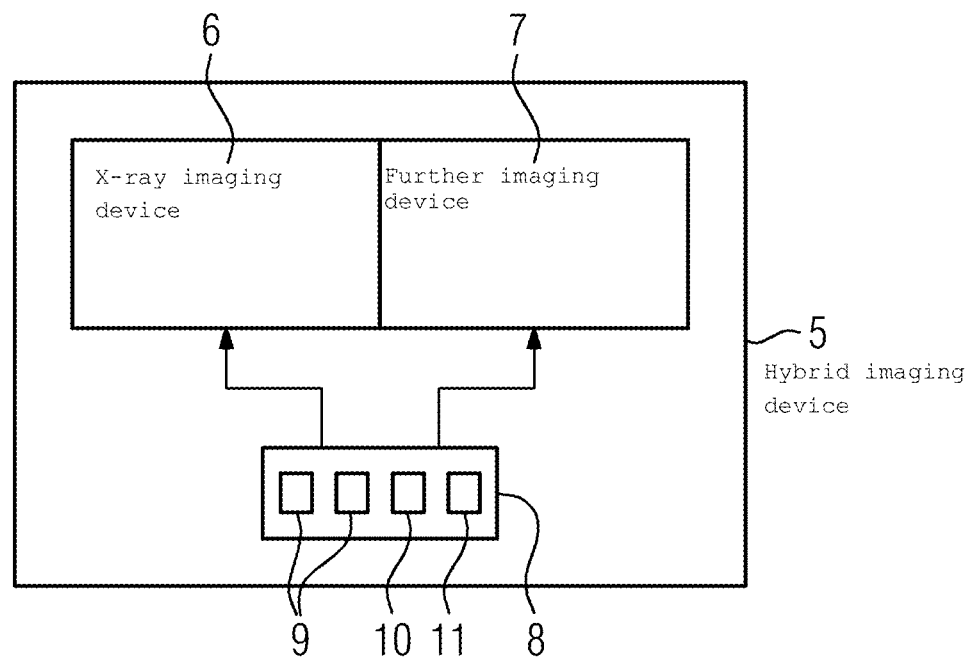

METHODS FOR PERFORMING DIGITAL SUBTRACTION ANGIOGRAPHY, HYBRID IMAGING DEVICES, COMPUTER PROGRAMS, AND ELECTRONICALLY READABLE STORAGE MEDIA

The application claims the benefit of European Patent Application No. EP 17185341.9, filed Aug. 8, 2017, which is hereby incorporated by reference in its entirety.

The activity leading to this application has received funding from the European Institute of Innovation and Technology (EIT) under grant agreement No. EIT/EIT HEALTH/SGA2017/1. This European body receives support from the European Union's Horizon 2020 research and innovation program.

TECHNICAL FIELD

The disclosure concerns a method for performing digital subtraction angiography of a region of interest of a patient, wherein, with a contrast agent being present in blood vessels of the region of interest, a filled image data set of the region of interest is acquired by x-ray imaging and an angiography image data set is created by subtracting a mask image data set from the filled image data set. The disclosure also concerns a hybrid imaging device, a computer program, and an electronically readable storage medium.

BACKGROUND

Digital subtraction angiography (DSA) is a well-known imaging technique, which may be used to visualize blood vessels of a patient in medical imaging. In a classical workflow, first a mask image data set without a contrast agent being present in the region of interest is acquired by x-ray imaging. In this mask image data set, blood vessels may hardly be distinguished from surrounding anatomical structures. Subsequently, a filled image data set of the region of interest is acquired with contrast agent being present in the blood vessels of the region of interest. In these x-ray images, the blood vessels are amplified, whereas the contrast of anatomical structures surrounding the contrast-enhanced blood vessels remains constant. To derive a DSA angiography image data set, the mask image data set, (e.g., the non-contrast-enhanced image), is subtracted from the filled image data set, (e.g., the contrast enhanced image data set). In this manner, the signal from surrounding anatomical structures, (e.g., tissue and bones), may be eliminated and the resulting image only shows the blood vessels. Digital subtraction angiography may be performed using three-dimensional image data sets, e.g., computer tomography (CT) image data sets and/or using two-dimensional image data sets such as projection images. In the case of projection images, the line integral of the mask image data set and the filled (e.g., contrast-enhanced) image data set are subtracted and the attenuation of the contrast-enhanced vessels may be obtained.

A known problem in digital subtraction angiography is the time difference between the acquisition of the mask image data set and the filled image data set, which makes this imaging technique prone to motion errors. It has thus been proposed to perform registration of the mask image data set and the filled image data set, like for example described in U.S. Pat. No. 8,023,732 and Y. Bentoutou et al., "An invariant approach for image registration in digital subtraction angiography", Pattern Recognition 35 (12) 2002, pages 2853-2865. Because blood vessels are soft-tissue structures, the appearing deformations are mostly of a non-rigid nature, complicating the process of registration. An additional problem is the time-consuming nature of the registration itself, which may not be desirable if the digital subtraction angiography is performed during an in particular minimally invasive intervention.

Another problem related to digital subtraction angiography is radiation exposure of the patient. To obtain one DSA angiography image data set, the patient is irradiated at least two times.

In an article by M. Unberath et al., "Virtual single-frame subtraction imaging", proceedings of the 4$^{th}$ CT Meeting (4$^{th}$ International Conference on Image Formation in X-Ray Computed Tomography), Bamberg, Germany, Jul. 18, 2016, pages 89 to 92, 2016, a virtual digital subtraction coronary angiography has been proposed. By vessel segmentation and background estimation, a virtual mask image useable for subtraction may be derived. However, assumptions and time-consuming image analysis are required, which may lead to inaccuracies and/or errors in the virtual mask image data set.

SUMMARY AND DESCRIPTION

The scope of the present disclosure is defined solely by the appended claims and is not affected to any degree by the statements within this description. The present embodiments may obviate one or more of the drawbacks or limitations in the related art.

It is an object to provide a method for digital subtraction angiography imaging, which reduces the amount of irradiation of the patient and provides improved image quality due to reduced motion artifacts.

In a method as initially described, a hybrid imaging device including an x-ray imaging device for x-ray imaging and a further imaging device for at least one additional imaging modality is used. The imaging devices are co-registered and operable to acquire image data in the same of field of view. The filled image data set is acquired using the x-ray imaging device, while simultaneously an anatomy data set is acquired using the further imaging device. The mask image data set is derived from the anatomy data set in a conversion process, which converts additional imaging modality image data into virtual x-ray image data.

Hybrid imaging devices, (e.g., a combined x-ray, in particular computer tomography (CT), and magnetic resonance (MR) imaging device (CT-MR-device)), have already been proposed in the state of the art, namely aiming at combining advantageous imaging properties of both modalities to gain additional information about a region of interest of the patient. An exemplary combined MR/x-ray-system is described in an article by R. Fahrig et al., "A truly hybrid interventional MR/X-ray system: feasibility demonstration", Journal of Magnetic Resonance Imaging 13 (2) 2001, pages 294-300.

Such a hybrid imaging device is used to realize single-shot DSA acquisitions by simultaneously acquiring the filled image data set, (e.g., by using the x-ray device), and simultaneously an anatomy image data set using the further imaging device, wherein a certain relationship between these modalities exists such that virtual x-ray image data may be derived from additional imaging modality image data, allowing to reconstruct/derive a virtual mask image data set from the anatomy image data set, which is not contrast-enhanced, e.g., the contrast agent used is only visible in x-ray imaging, not in additional modality imaging.

The term "simultaneous" may be broadly understood in the sense that at least no motion occurs between the acquisition of the two image data sets. While simultaneous acquisition thus at least covers truly parallel imaging, (e.g., acquiring x-ray image data at least temporarily at the same time as further the modality image data), interleaved acquisitions as well as acquisitions immediately adjacent in time may also be understood as simultaneous. The acquisition of contrast-enhanced images is prepared by administering an x-ray contrast agent into the region of interest and then acquiring the desired x-ray projection images to generate the filled image data set, which may also be termed contrast-enhanced image data set. The filled image data set shows amplified, (e.g., contrast-enhanced), blood vessels including surrounding anatomical structures. Contrarily to common approaches, however, the mask image data set without contrast-enhanced blood vessels is not acquired using the x-ray device. Instead, the mask image data set is derived from an anatomy image data set acquired simultaneously in the hybrid imaging device. The mask image data set is to be formed in a way such that only the unwanted, surrounding anatomical structures are visible or blood vessels and surrounding anatomical structures show similar contrasts. By subtracting the mask image data set from the filled image data set, unwanted anatomical structures, (e.g., tissues and bones), are removed and the angiography image data set showing only the contrast-enhanced blood vessels is obtained. As the image data sets have been acquired simultaneously, e.g., in at least the same motion state of the patient, no registration or only little registration of both image data sets is needed to perform subtraction and obtain an angiography image data set of high quality.

In order to perform the conversion process, a mapping between both modalities is necessary. As a result of the conversion process, the absolute intensities of both image data sets, (e.g., the filled image data set and the mask image data set), is in the same value range for the same anatomical structures in order to perform a subtraction with appropriate results. Magnetic resonance imaging may be used as the additional imaging modality. In the state of the art, it has already been proposed to estimate x-ray attenuation values from magnetic resonance image data in the context of PET-MR radio therapy, (cf., for example, M. Kapanen et al. "T1/T2*-Weighted MRI Provides Clinically Relevant Pseudo-CT Density Data for the Pelvic Bones in MRI-only Based Radiotherapy Treatment Planning", Acta Oncologica 52 (3) 2013, pages 612 to 618; or B. K. Navalpakkam et al., "Magnetic Resonance-Based Attenuation Correction for PET/MR Hybrid Imaging Using Continuous Valued Attenuation Maps", Investigative Radiology 48 (5) 2013, pages 323-332). Using such a mapping in a hybrid imaging device, however, has the advantage that, when training the conversion process, a ground truth mapping is available and may be generated "on the fly". Thus, mapping from the additional imaging modality, (e.g., magnetic resonance), to x-ray of a quality high enough for digital subtraction angiography is possible. The method may be applied to two-dimensional (2D) DSA as well as to three-dimensional (3D) DSA. In the two-dimensional case, the line integrals are subtracted and therefore, the attenuation of the contrast-enhanced vessels is preserved. In the two-dimensional case, where forward projections may be performed to obtain the mask image data set, the anatomy image data set may cover the whole patient at least in projection directions used in the filled image data set. However, in some cases, it may be feasible to add missing data from a patient model and/or anatomic data bases.

The herein proposed single-shot DSA acquisition using a hybrid imaging device has several advantages. By generating the mask image data set using an x-ray free imaging modality, the overall radiation exposure of the patient may be reduced. Additionally, simultaneous imaging prevents or at least attenuates problems related to motion between the respective acquisitions. This eliminates the need for complex image registration methods and reduces the overall time needed to obtain angiography image data sets.

Reducing the overall radiation exposure for the patient and the clinical staff is a key issue in medical imaging. With the proposed approach, this may be achieved for digital subtraction angiography, which is a frequently used technique in the interventional as well as the diagnostic environment. Simultaneously, the time spent for a single DSA acquisition may be reduced. This, in turn, not only improves the status of digital subtraction angiography, but also provides a new field of application for hybrid imaging devices.

It is possible to derive the virtual x-ray image data of the mask image data set from the anatomy image data set using a theoretical framework, like, for example, described in the above-mentioned articles by Kapanen or Navalpakkam. However, the possibility to obtain ground truth data as training data predestines the method for the use of machine learning techniques.

Thus, an embodiment provides that the conversion process includes the application of a hybrid imaging device specific artificial intelligence conversion algorithm, which has been trained by machine learning using training data acquired with the hybrid imaging device, wherein x-ray ground truth data are acquired simultaneously with additional modality input data. Deep learning techniques may be employed. It is, however, also possible to take into account a basic knowledge on the physical relation between the respective image data/modalities when choosing the artificial intelligence conversion algorithm, a training algorithm, and/or algorithm parameters. In this embodiment, the disclosure takes advantage of the availability of high-quality ground truth data from the x-ray device, which, due to simultaneous imaging also for the training data, provides a high-quality foundation for deriving the artificial intelligence conversion algorithm and/or its parameters. Thus, an increased accuracy of the image data mapping in the conversion process may be achieved.

It is noted that the artificial intelligence conversion algorithm uses at least the additional modality image data and the additional modality acquisition parameters, which are relevant for the conversion, as input data. However, as further explained below, additional input data may be used in a corresponding input data set.

Image data sets of the training data may be decomposed into image patches, on which the training is performed. Thus, while learning the relations between the different modality input data, a localized approach is possible, reducing the amount of data to be processed during the training and leading nonetheless to reliable results for the conversion.

In an embodiment, the output data of the artificial intelligence conversion algorithm includes x-ray attenuation values for the region of interest imaged in the filled image data set, wherein the mask image data set is derived from the attenuation values by simulating x-ray imaging using the acquisition parameters used for acquiring the filled image data set. In particular, the herein mentioned simulation may include forward projection if two-dimensional image data are to be subtracted. In particular, the x-ray attenuation values may correspond to values in computer tomography data sets (e.g., CT values), as known from previous approaches as "pseudo-CT". The attenuation values may include all information needed to simulate or derive x-ray image data actually needed in the mask image data set.

It is, of course, also possible to include the acquisition parameters of the filled image data set into an input data set of the artificial intelligence conversion algorithm and immediately receive the mask image data set, in particular as corresponding virtual projection images. However, it may be easier to perform forward projection based on attenuation values than increasing the number of input parameters and integrating the forward projection into the conversion algorithm.

An input data set of the artificial intelligence conversion algorithm and the training data may also include patient parameters describing properties of the patient. In this manner, the accuracy of the conversion process may be further improved, as properties influencing the acquisition of image data of the patient may also be taken into account in the learning process. For example, the size of a patient may have effects on homogeneity of a B0 field of a magnetic resonance device and/or the amount of attenuation of x-rays passing through the patient.

It is noted that, in a concrete embodiment, the artificial intelligence conversion algorithm may already perform and thus include the subtraction act, yielding the angiography image data set as output.

The method may be further improved if the mask image data set is fine-corrected using non-contrast-enhanced image data of the filled image data set. At least areas of the filled image data set may be free of contrast-enhanced blood vessels such that the corresponding image values of the virtual mask image data set and the filled image data set may, in the theoretical perfect case, be identical.

These non-contrast-enhanced image values may, at least partly, be identifiable, such that such a comparison may be performed to derive corrections for a preliminary virtual mask image data set, for example, provided by the artificial intelligence conversion algorithm. That is, x-ray data of the filled image data set which present a ground truth for the current conversion process may be identified and used to adjust the preliminary virtual mask image data set or, in other words, the pre-trained mapping. An increased accuracy of the value conversion may be achieved. Different concrete methods or algorithms may be used to identify such ground truth segments of the filled image data. For example, blood vessels may be automatically segmented by using thresholds or the like, or histogram-based segmenting may be performed. It is noted that, because the x-ray image data and the additional modality data are acquired simultaneously, corresponding information for each motion state of the patient is available, which may be used to distinguish blood vessels from surrounding anatomical structures of the patient. In summary, an advantageous refinement of the virtual mask image data set may be achieved.

The disclosure further concerns a hybrid imaging device, including an x-ray imaging device for x-ray imaging and a further imaging device for at least one additional imaging modality, wherein the imaging devices are co-registered and operable to acquire image data in the same field of view, further including a control device configured to perform a method as disclosed herein. All explanations and features relating to the method may correspondingly be applied to the hybrid imaging device, providing the same advantages.

In particular, the control device may thus include at least one acquisition unit for controlling image acquisition for each modality, a conversion unit performing the conversion process and/or a digital subtraction angiography unit for determining the angiography image data set. Further functional units may be provided to implement further features as laid out above.

A computer program may be loaded into a storage device of a control device of a hybrid imaging device and includes program code to perform the acts of a method when the computer program is executed in the control device of the hybrid imaging device.

The computer program may be stored on an electronically readable storage medium, which thus includes electronically readable control information stored thereon, including a computer program and configured to perform a method disclosed herein if the electronically readable storage medium is used in a control device of a hybrid imaging device. The storage medium may be a non-transient storage medium, for example, a CD-ROM.

BRIEF DESCRIPTION OF THE DRAWINGS

Further details and advantages of the disclosure may be taken from the following description of certain embodiments in conjunction with the drawings, wherein:

FIG. 1 depicts a flow chart of an embodiment of the method.

FIG. 2 depicts an embodiment of a hybrid imaging device.

DETAILED DESCRIPTION

FIG. 1 depicts the acquisition of a digital subtraction angiography image data set according to an embodiment. A hybrid imaging device is used, in this embodiment a CT-MR-device, which includes an x-ray device, (e.g., a CT device), and as a further imaging device a magnetic resonance device, wherein these imaging devices are configured to be able to acquire image data of both modalities simultaneous and in the same field of view. In the following, an angiography image data set of blood vessels of a patient in a region of interest is to be obtained by single shot DSA imaging.

In the past, act S1 has already been performed, namely the training of an artificial intelligence conversion algorithm, which converts (or, in other words, maps) magnetic resonance image data acquired with the hybrid imaging device to x-ray image data. The training is performed by machine learning, in this embodiment using deep learning techniques, using training data, including image data of both modalities acquired simultaneously, in particular without the use of any contrast agent. The image data of both modalities, the acquisition parameters and optionally also patient data are combined to form the training data, which is used by a training algorithm to create and parametrize the artificial intelligence conversion algorithm, which, in this case, receives magnetic resonance image data and corresponding relevant acquisition parameters for the magnetic resonance image data (and, optionally, patient data) as an input data set and puts out virtual x-ray image data, which matches the x-ray image data provided as training data for the corresponding training input data set. The x-ray image data of the training data thus provide the ground truth.

During training, the image data sets of the training data are split into image patches for more efficient learning.

The virtual x-ray data output by the artificial intelligence conversion algorithm are, in this case, attenuation values such as calculated in a CT image data set. If projection images are required, the x-ray imaging may be simulated, forward projecting to the region of interest. Just like forward projection, other calculation/simulation approaches may be used to generate x-ray image data fitting the specified acquisition parameters for the x-ray device.

It is of course possible to update the training any time new training data are available.

For a concrete patient to be examined with the hybrid imaging device, in acts S2a and S2b, which are performed simultaneously, after a contrast agent has been administered to the patient, which may only be seen in x-ray imaging, a filled image data set 1 is acquired using the x-ray imaging device and, in parallel, an anatomy image data set 2 is acquired using the magnetic resonance imaging device. Both image data sets 1, 2 show the region of interest. The filled image data set 1 contains contrast-enhanced blood vessels, wherein these are imaged normally without the contrast agent having an effect in the anatomy image data set 2.

In act S3, during a conversion process, the anatomy image data set 2 and its relevant acquisition parameters are used as an input data set for the artificial intelligence conversion algorithm, such that, possibly after simulating the x-ray imaging process using the acquisition parameters of the filled image data set 1, a virtual mask image data set 3 is obtained, which may have been refiningly corrected using identifiable ground truth data of the filled image data set 1 in an optional act S4.

In act S5, the mask image data set 3 may be subtracted from the filled image data set 1, as known in digital subtraction angiography, to obtain the angiography image data set 4.

FIG. 2 depicts a simplified drawing of a hybrid imaging device 5. The hybrid imaging device includes an x-ray imaging device 6, (e.g., a CT device), and a further imaging device 7, (e.g., a magnetic resonance imaging device). In a concrete realization of the hybrid imaging device 5, parts of the magnetic resonance imaging device may for example be split, (e.g., a gradient coil arrangement), to provide room for the gantry of the CT device. Other constructions are also conceivable.

Both imaging devices 6, 7 are controlled by are shared control device 8, which is also configured to perform a method as disclosed herein. In this respect, among other components, the control device 8 includes acquisition units 9 for both modalities, a conversion unit 10 for realizing the conversion process and a digital subtraction angiography unit 11 for obtaining the angiography image data set 4.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for performing digital subtraction angiography of a region of interest of a patient, wherein, with a contrast agent being present in blood vessels of the region of interest, the method comprises:

acquiring a filled image data set and an anatomy image data set of the region of interest by x-ray imaging using a hybrid imaging device comprising an x-ray imaging device and a further imaging device for at least one additional imaging modality, wherein the x-ray imaging device and the further imaging device are co-registered and configured to acquire x-ray image data and additional imaging modality image data, respectively, in a similar field of view, and wherein the filled image data set and the anatomy image data set are acquired by simultaneously using the x-ray imaging device and the further imaging device;

deriving a mask image data set from the anatomy image data set in a conversion process that converts the additional imaging modality image data into virtual x-ray image data; and creating an angiography image data set by subtracting the mask image data set from the filled image data set.

2. The method of claim 1, wherein the conversion process comprises an application of an artificial intelligence conversion algorithm, which has been trained by machine learning using training data acquired with the hybrid imaging device, and wherein x-ray ground truth data are acquired simultaneously with additional modality input data.

3. The method of claim 2, further comprising:

decomposing image data sets of the training data into image patches, on which the training is performed.

4. The method of claim 3, wherein output data of the artificial intelligence conversion algorithm comprises x-ray attenuation values for the region of interest imaged in the filled image data set, and wherein the mask image data set is derived from the x-ray attenuation values by simulating x-ray imaging using acquisition parameters used for acquiring the filled image data set.

5. The method of claim 4, wherein an input data set of the artificial intelligence conversion algorithm and the training data also comprise patient parameters describing properties of the patient.

6. The method of claim 2, wherein output data of the artificial intelligence conversion algorithm comprises x-ray attenuation values for the region of interest imaged in the filled image data set, and wherein the mask image data set is derived from the x-ray attenuation values by simulating x-ray imaging using acquisition parameters used for acquiring the filled image data set.

7. The method of claim 6, wherein an input data set of the artificial intelligence conversion algorithm and the training data also comprise patient parameters describing properties of the patient.

8. The method of claim 2, wherein an input data set of the artificial intelligence conversion algorithm and the training data also comprise patient parameters describing properties of the patient.

9. The method of claim 1, further comprising:

correcting the mask image data set using non-contrast-enhanced image data of the filled image data set.

10. The method of claim 1, wherein the at least one additional imaging modality comprises magnetic resonance imaging.

11. A hybrid imaging device comprising:

an x-ray imaging device for x-ray imaging;

a further imaging device for at least one additional imaging modality, wherein the x-ray imaging device and the further imaging device are co-registered and configured to acquire image data in a same field of view; and a control device configured to:
  acquire a filled image data set and an anatomy image data set of a region of interest using the x-ray imaging device and the further imaging device by simultaneously using the x-ray imaging device and the further imaging device;
  derive a mask image data set from the anatomy image data set in a conversion process that converts additional imaging modality image data into virtual x-ray image data; and
  create an angiography image data set by subtracting the mask image data set from the filled image data set.

12. A computer program, which, when executed on a control device of a hybrid imaging device, is configured to:
  acquire a filled image data set and an anatomy image data set of a region of interest using an x-ray imaging device and an further imaging device of the hybrid imaging device by simultaneously using the x-ray imaging device and the further imaging device;
  derive a mask image data set from the anatomy image data set in a conversion process that converts additional imaging modality image data into virtual x-ray image data; and
  create an angiography image data set by subtracting the mask image data set from the filled image data set.

13. The method of claim 1, wherein the further imaging device is a magnetic resonance device.

14. The hybrid imaging device of claim 11, wherein the at least one additional imaging modality comprises magnetic resonance imaging.

15. The hybrid imaging device of claim 11, wherein the further imaging device is a magnetic resonance device.

* * * * *